(12) United States Patent
Rella

(10) Patent No.: US 9,274,031 B1
(45) Date of Patent: Mar. 1, 2016

(54) GAS ANALYSIS SYSTEM PROVIDING SIMULTANEOUS ANALYSIS AND MULTI-POINT SAMPLE ACQUISITION

(71) Applicant: Picarro, Inc., Santa Clara, CA (US)

(72) Inventor: Chris W. Rella, Sunnyvale, CA (US)

(73) Assignee: Picarro, Inc., Santa Clara, AZ (US)

( * ) Notice: Subject to any disclaimer, the term of this patent is extended or adjusted under 35 U.S.C. 154(b) by 316 days.

(21) Appl. No.: 13/866,637

(22) Filed: Apr. 19, 2013

Related U.S. Application Data

(60) Provisional application No. 61/635,793, filed on Apr. 19, 2012.

(51) Int. Cl.
  *G01N 1/22* (2006.01)
  *G01N 1/26* (2006.01)

(52) U.S. Cl.
  CPC .................................... *G01N 1/26* (2013.01)

(58) Field of Classification Search
  CPC ...... G01N 1/22; G01N 2001/002; G01N 1/26
  USPC ........ 73/23.2, 23.41, 863.31, 863.33, 863.83, 73/864.81
  See application file for complete search history.

(56) References Cited

U.S. PATENT DOCUMENTS

| | | | | |
|---|---|---|---|---|
| 3,653,840 A | * | 4/1972 | Silas | 436/142 |
| 3,765,247 A | * | 10/1973 | Riggs | 73/863.23 |
| 3,827,302 A | * | 8/1974 | Sato | 73/863.33 |
| 3,846,075 A | * | 11/1974 | Cioffi | 422/81 |
| 4,090,392 A | * | 5/1978 | Smith et al. | 73/863.23 |
| 4,399,688 A | * | 8/1983 | Dennis | 73/23.35 |
| 4,704,910 A | * | 11/1987 | Conrad | 73/863.21 |
| 5,162,652 A | * | 11/1992 | Cohen et al. | 250/288 |
| 5,691,487 A | * | 11/1997 | Green et al. | 73/863.86 |
| 6,094,968 A | * | 8/2000 | Scheufler et al. | 73/23.2 |
| 6,629,043 B1 | * | 9/2003 | Poteat | 702/51 |
| 7,383,718 B2 | * | 6/2008 | McCurry et al. | 73/23.4 |
| 7,597,014 B2 | | 10/2009 | Tans | |
| 7,856,899 B2 | * | 12/2010 | Furtaw et al. | 73/864.73 |
| 2002/0144537 A1 | * | 10/2002 | Sharp et al. | 73/31.01 |
| 2006/0283269 A1 | * | 12/2006 | Anderson et al. | 73/863.31 |
| 2010/0094565 A1 | * | 4/2010 | Prince et al. | 702/22 |

* cited by examiner

*Primary Examiner* — Daniel S Larkin
(74) *Attorney, Agent, or Firm* — Lumen Patent Firm

(57) ABSTRACT

A gas handling system capable of simultaneous sample analysis and multi-point sample acquisition is provided. An exemplary system has N gas inlets and N+1 sample storage loops (having a high aspect ratio), where N≥2. The high aspect ratio of the sample storage loop prevents significant sample diffusion along the length of the loop. Therefore each loop preserves a time axis for its contents. The sample loops can be disposed to simultaneously admit samples from different points in space. A gas switching manifold can be employed to connect the sample storage loops sequentially and one at a time to the gas analysis instrument for analysis. A common time axis for all samples can be reconstructed from the switching and flow conditions. Thus a simultaneous multi-point measurement using a single analysis instrument is provided.

11 Claims, 12 Drawing Sheets

GAS ANALYSIS SYSTEM PROVIDING SIMULTANEOUS ANALYSIS AND MULTI-POINT SAMPLE ACQUISITION

CROSS REFERENCE TO RELATED APPLICATIONS

This application claims the benefit of U.S. provisional patent application 61/635,793, filed on Apr. 19, 2012, and hereby incorporated by reference in its entirety.

FIELD OF THE INVENTION

This invention relates to gas handling for measurements.

BACKGROUND

Measurements of gaseous species in air are of considerable interest for applications such as environmental monitoring etc. However, it can be difficult to perform such measurements accurately and inexpensively. Most emissions sources will result in a plume of the species of interest being emitted into the atmosphere, with the direction and spread of the plume being determined in complex and highly variable manner by the (turbulent) transport of the atmosphere. A single-point measurement is not likely to provide an accurate estimate of the total emission in the plume, and multiple sequential measurements at different locations are subject to errors caused by motion of the plume (e.g., as local wind conditions vary). Simultaneous measurements using an analyzer at each measurement location can address this issue, but this approach has the disadvantage of being costly (i.e., expensive analyzer hardware is duplicated).

SUMMARY

These problems are addressed in the present approach by providing a sample handling system that can simultaneously perform sample analysis and multi-point sample acquisition. An exemplary system has multiple sample storage loops. Each sample storage loop is a long, thin tube (or similar high aspect ratio configuration) that is capable of admitting a sample from an ambient environment, and is capable of providing its contents to an analysis instrument. These sample storage loops can be regarded as being analogous to audio recording tapes, where the step of admitting a sample from ambient is a "recording" step, and the step of providing the sample loop contents to the analysis instrument is a "playback" step. The high aspect ratio of the sample storage loop prevents significant sample diffusion along the length of the loop (provided that both recording and playback are completed sufficiently quickly). Therefore, the analogy to audio recording and playback extends to the notion of a time axis for the gaseous samples in the sample storage loops (i.e., each loop preserves a time axis for its contents).

A further important feature of the present approach is that "playback" and "recording" need not be at the same speed—playback can be either faster or slower than recording. Again, this is completely analogous to audio recording on a tape. Thus, recording can be performed at a speed suitable for sample gathering, and playback can be performed at a flow rate suitable for the gas analysis technique being employed.

This technology can address the above identified problems by providing three or more sample storage loops connected to a single analysis instrument for measuring two or more measurement points, where the sample loops are disposed to simultaneously admit samples from different points in space (horizontally and/or vertically separated). There is one more sample storage loop than there are independent measurement points, so that playback can occur on one loop while the remaining loops are recording the data from the measurement points. Such simultaneously obtained samples can provide accurate results for an emission plume. A gas switching manifold can be employed to connect the sample storage loops sequentially and one at a time to the gas analysis instrument for analysis. A common time axis for all samples can be reconstructed from the switching and flow conditions.

Since only a single analysis instrument is needed, the cost is greatly reduced compared to multi-point approaches with an analysis instrument on each channel. The ability to provide a common time axis for the gas samples effectively makes the present approach a simultaneous multi-point measurement using a single analysis instrument, which is a considerable advance in the art.

DETAILED DESCRIPTION

Figure 1A:
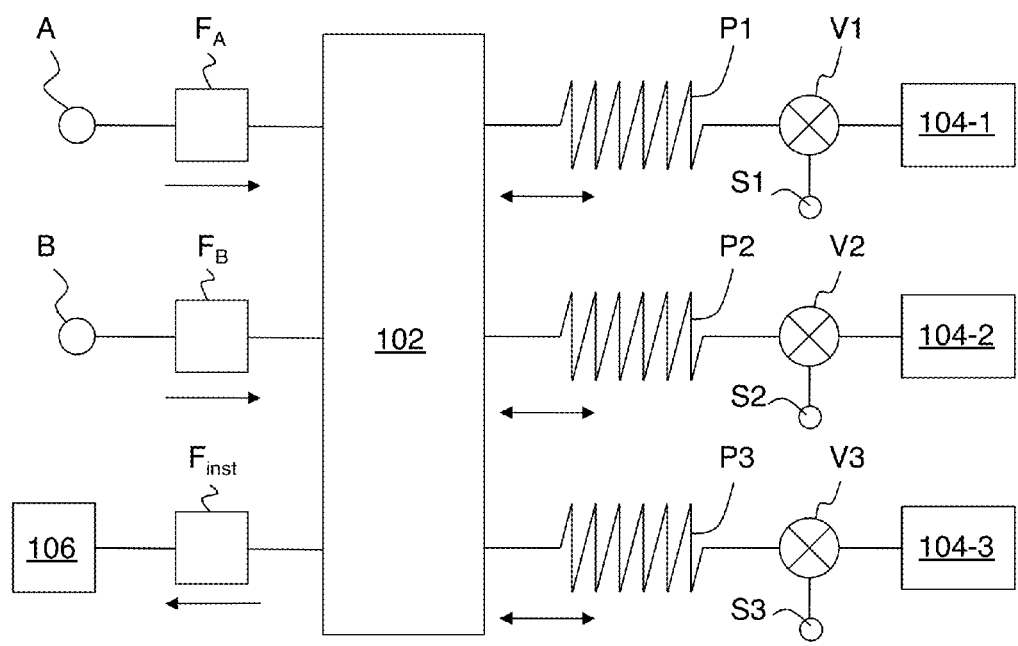
FIG. 1A shows an exemplary embodiment of the invention.

FIG. 1A shows an exemplary embodiment of the invention. In this example, two gas sample inlets A and B are disposed at spaced apart locations. Three gas sample storage chambers are present (P1, P2, and P3), as is a gas analysis instrument 106. Practice of the invention does not depend critically on details of gas analysis instrument 106. Any gas analysis instrument can be employed, including but not limited to optical gas analysis instruments based on cavity-enhanced spectroscopic techniques, such as cavity enhanced absorption spectroscopy (CEAS), cavity ring-down spectroscopy (CRDS), etc.

These components are connected to each other via a gas flow control manifold 102 that is capable of connecting the gas storage chambers to the gas sample inlets and to the gas analysis instrument. More specifically, the gas flow control manifold is capable at least of connecting any of the gas sample storage chambers to the gas analysis instrument while at least one other of the gas sample storage chambers is connected to one of the gas sample inlets. Pumps 104-1, 104-2 and 104-3 are used to draw gas samples into the corresponding gas sample storage chambers P1, P2, and P3 respectively. Gas sources S1, S2 and S3 are used to provide feed gas when performing analysis of the contents on P1, P2 and P3 (respectively) in gas analysis instrument 106. As indicated above, it is convenient to refer to sample acquisition as "recording" and sample analysis as "playback". Valves V1, V2 and V3 are used to switch each gas sample storage chamber between the recording and playback modes. Usually, one of the chambers is in playback mode, and all others are in recording mode.

Figure 1B:
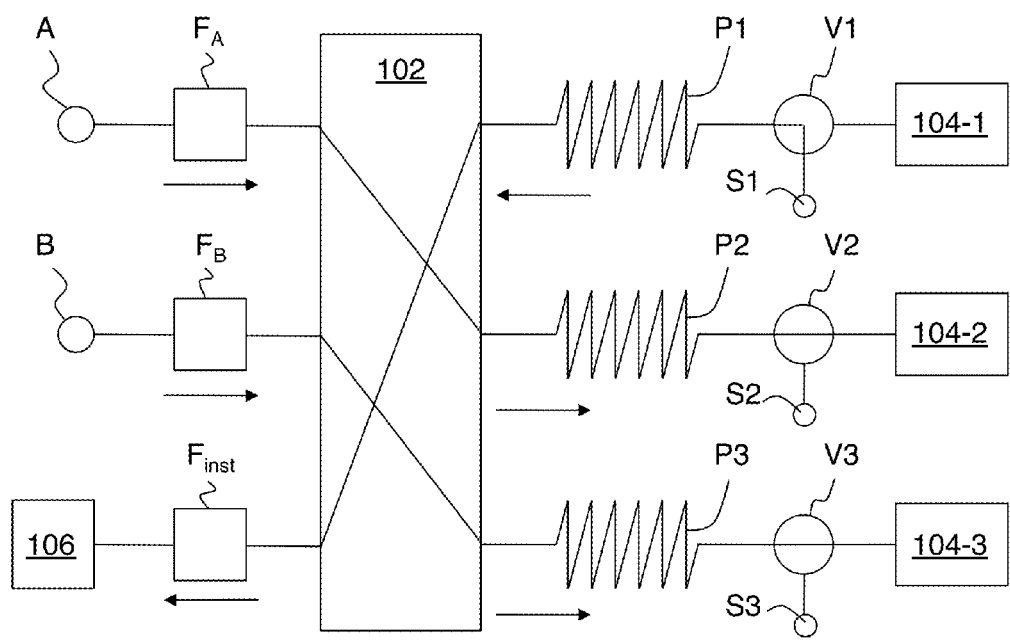
FIG. 1B shows one of the states of the example of FIG. 1A.

FIG. 1B shows one of the states of the example of FIG. 1A. Here we see that chamber P2 is in recording mode for inlet A, chamber P3 is in recording mode for inlet B, and chamber P1 is in playback mode, having its contents provided to gas analysis instrument 106. The example of these figures has two gas inlets, but the number of gas inlets can be greater than two. In general, this approach is applicable to N gas sample inlets disposed at spaced apart locations, where N is an integer greater than or equal to two. In this general case, there are N+1 gas sample storage chambers, and the gas flow control manifold connects the N+1 gas sample storage chambers to N gas inlets and one gas analysis instrument.

In some cases, the gas flow rate for recording and playback is different. More specifically, let $f_q$ be the acquisition gas flow rate (recording rate) and let $f_a$ be the analysis flow rate (playback rate). Then it is preferred for the acquisition flow rate and the analysis flow rate to differ by 40% or more of the acquisition flow rate (i.e., $|f_a - f_q| > 0.4\, f_a$). As described in greater detail below, it is often preferred for the playback flow rate to be N times the recording flow rate, where N is the number of gas sample inlets. In general, however, the analysis flow rate can be greater than or less than the acquisition flow rate.

Preferably, the gas sample storage chambers are configured as tubes having a length to diameter ratio of 100 or more. Such tubes effectively provide a gas recording of the inlets, because diffusion along the length of such a tube can be made negligible during the total time for a recording and playback cycle. This condition will be satisfied if the total recording and playback cycle time is substantially less than a diffusion time for gas along the length of the gas sample storage chambers. Methods for estimating such diffusion times are known in the art.

Figure 2:
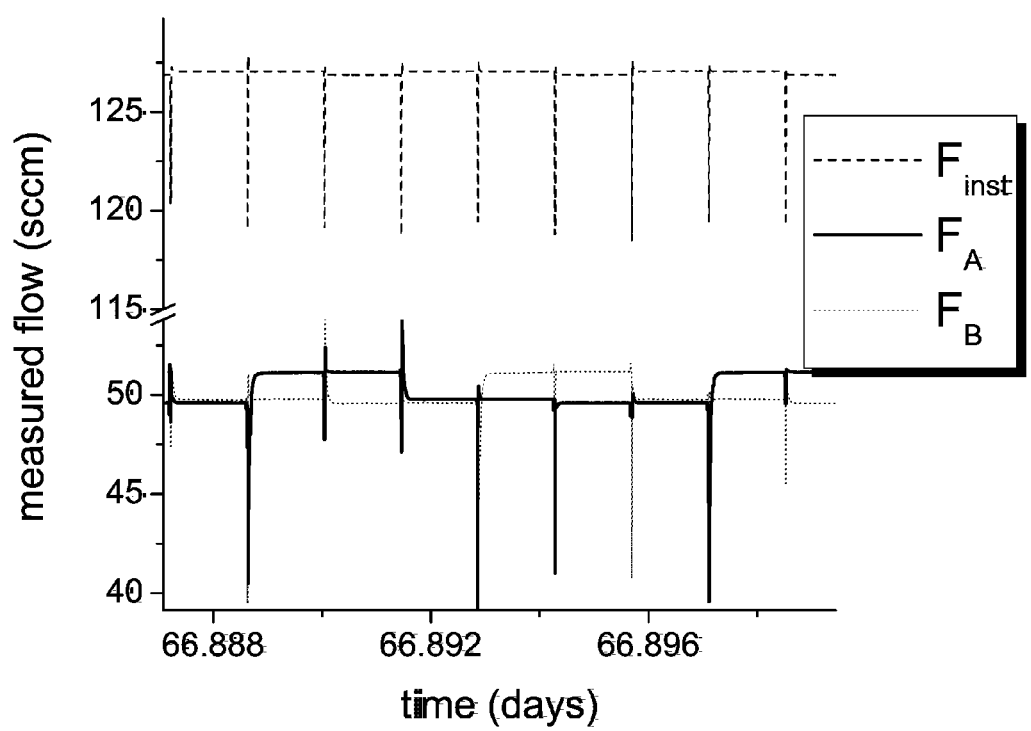
FIG. 2 provides an example of measured flow rates.

Optionally, gas flow rate meters $F_A$, $F_B$ and $F_{inst}$ are present at the gas sample inlets A and B, and at the inlet of gas analysis instrument 106. The purpose of such flow meters, if present, is to provide measured flow rate information for use in reconstructing a common time axis for multiple gas samples. FIG. 2 provides an example of measured flow rates. Here measured flow rates at two sample inlets and a gas analysis instrument inlet are shown during operation of an exemplary system.

Figures 3A, 3B:
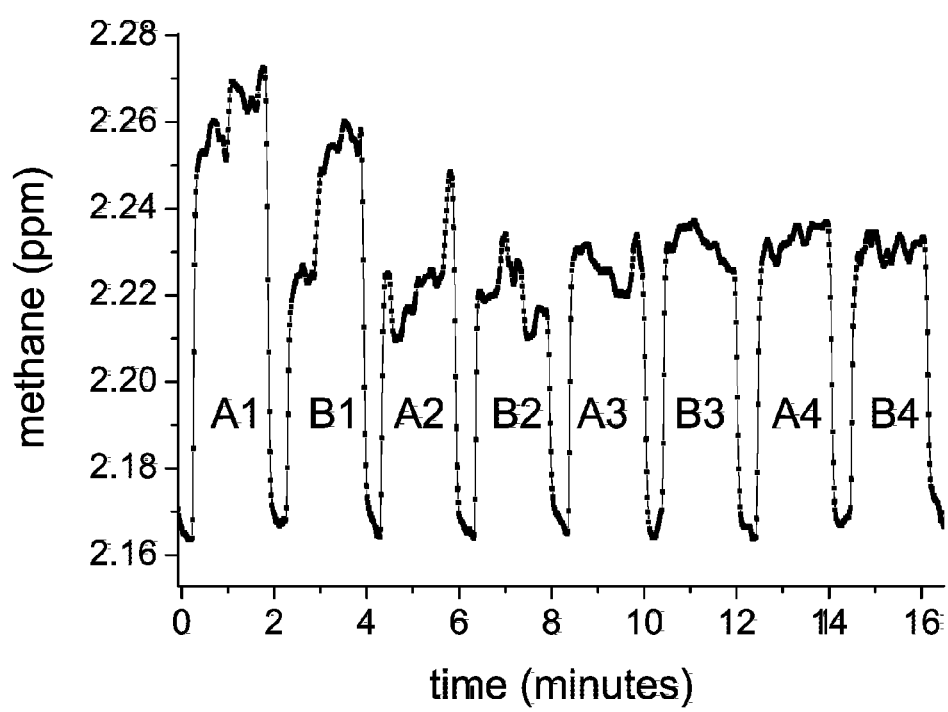
FIGS. 3A-B provide an example of gas sample playback.

FIGS. 3A-B provide an example of gas sample playback. In this example, gas inlets A and B were actually at the same location (in order to provide a baseline test of the system). Here a gas sample including methane was sampled at co-located (but otherwise independent) inlets A and B, with relative timing as shown on FIG. 3A. Playback of the samples gives the results of FIG. 3B. The sharp drops in measured methane concentrations seen on FIG. 3B are an artifact based on the use of room air (not containing methane) as the playback fill gas (e.g., gas source S1 on FIG. 1B). When this gas, not containing methane, reaches instrument 106, the measured methane concentration drops. Such artifacts can be eliminated by appropriately adjusting the timing of recording and playback. Here, however, these artifacts helpfully distinguish the A playback from the B playback, making the consistency of the A and B results immediately apparent from FIG. 3B.

Figure 4A:
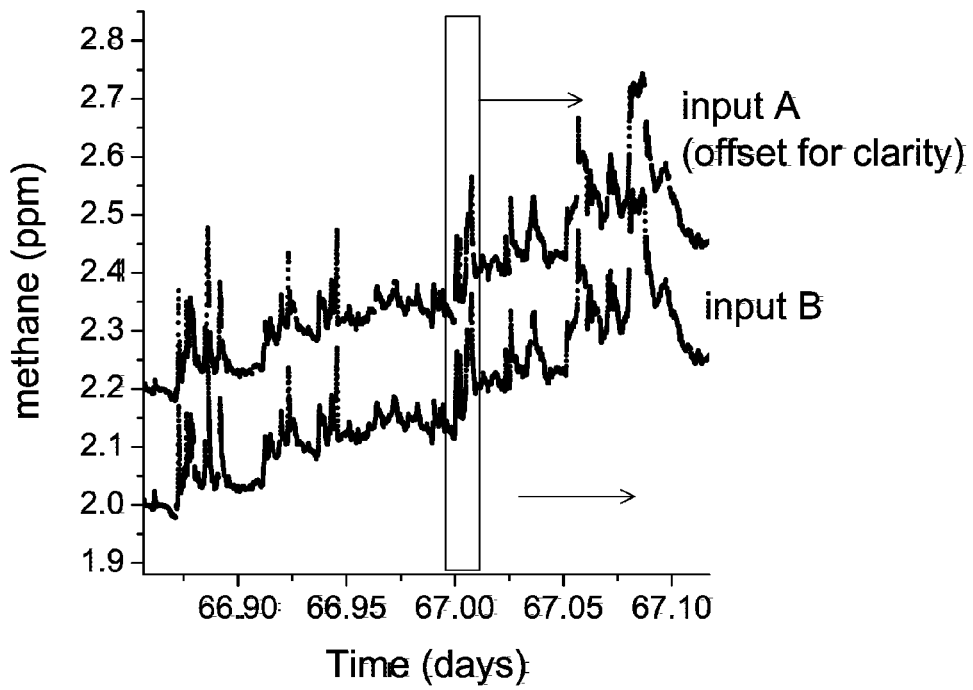
FIGS. 4A-B provides an example of reconstructing a common time axis for multiple gas samples.
Figure 4B:
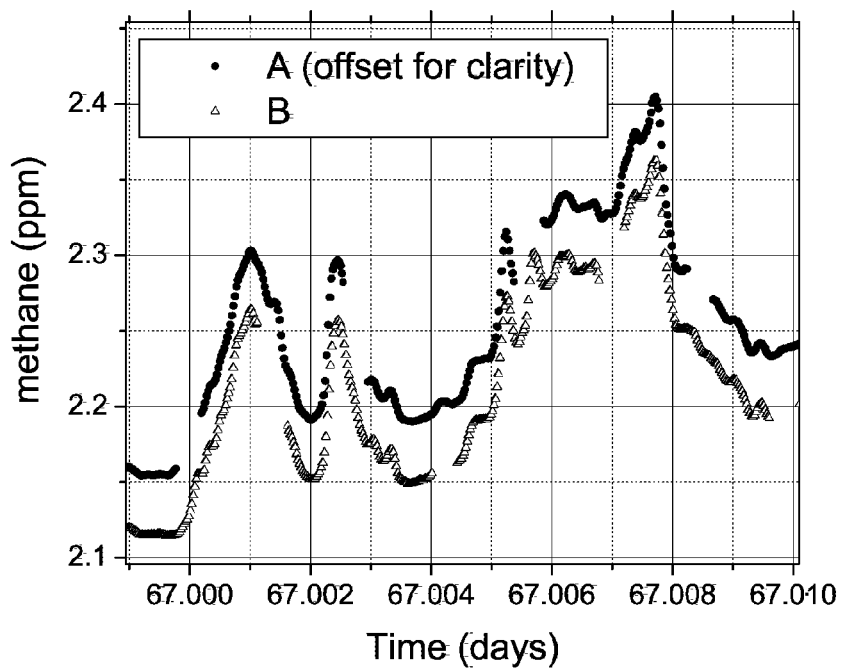

Further evidence for consistency is seen from FIGS. 4A-B, which provide an example of reconstructing a common time axis for multiple gas samples. Here playback of the A and B samples (from co-located A and B inlets) is shown using a common time axis reconstructed from the measured flow rates and knowledge of the valve states. The results for inlets A and B coincide on FIGS. 4A-B, but are show offset from each other for clarity. FIG. 4B shows an enlarged view of the indicated section of FIG. 4A. This time axis reconstruction is good to about 1-2 seconds and about 1-2 parts per billion in concentration. No free parameters are used in the time axis reconstruction. Measured flow rates (e.g., as on FIG. 2) and known valve states, combined with the molar volumes of the various connections in the system (which are assumed to be known from the system design), provide all information required for the time axis reconstruction. Relevant connections here include the connections between the gas inlets and the gas flow control manifold, connections within the gas flow control manifold, and connections between the gas flow control manifold and the gas analysis instrument.

In general, any way of controlling the gas flows so as to provide recording and playback as described above can be used to practice the invention. However, there are some practical considerations that lead to preferred embodiments. More specifically, it is preferred for all states of the system to have N channels recording and one channel playing back, and to switch periodically among these states without the need for any significant pauses to accommodate a flow rate mismatch between recording and playback. Such pauses are highly undesirable in view of the tendency of gas diffusion in the samples to reduce time resolution of the samples. If unnecessary pauses are made in operation, these pauses reduce the time resolution for no good reason. It is also desired for recording to nominally fill a gas sample storage chamber and for playback to nominally empty the gas sample storage chamber. (More precisely, the gas sample storage chambers get filled with the feed gas during playback.) These considerations lead to the above stated preference that the playback rate be N times the recording rate where N is the number of gas sample inlets.

Figure 5A:
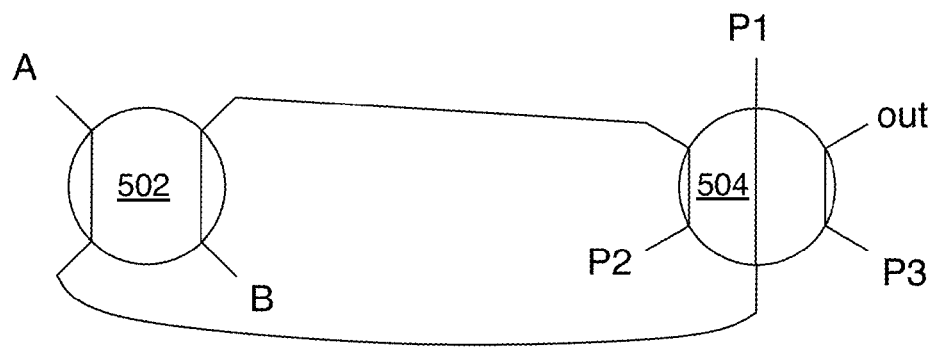
FIGS. 5A-F provide an example of a preferred gas flow switching approach for two gas sample inlets.
Figure 5B:
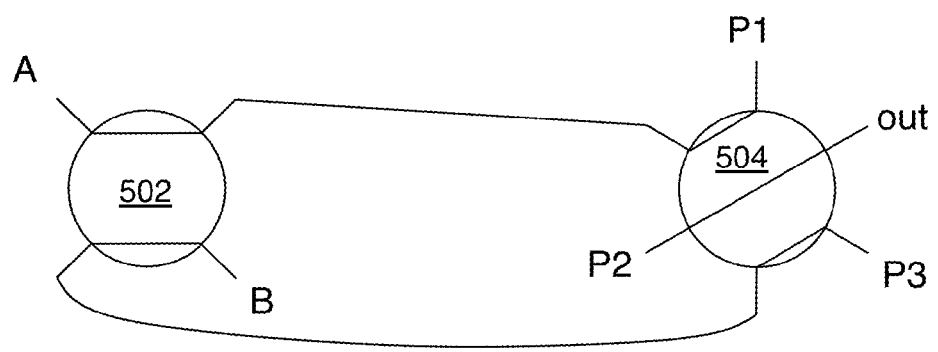
Figure 5C:
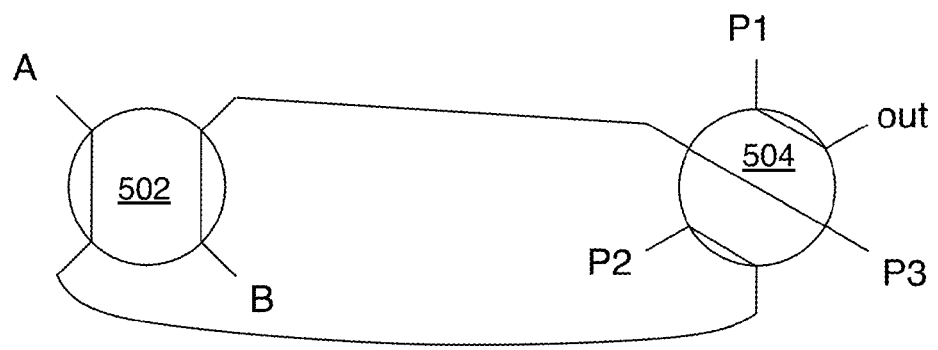
Figure 5D:
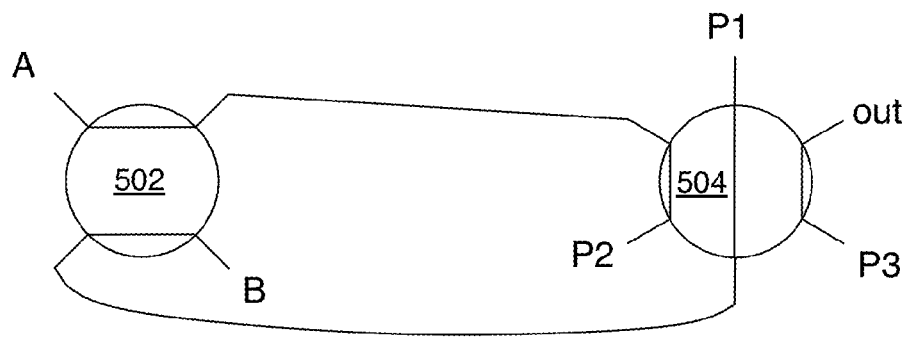
Figure 5E:
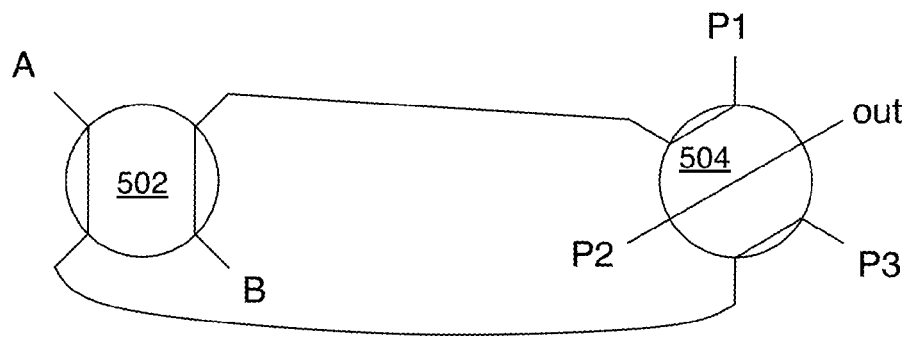
Figure 5F:
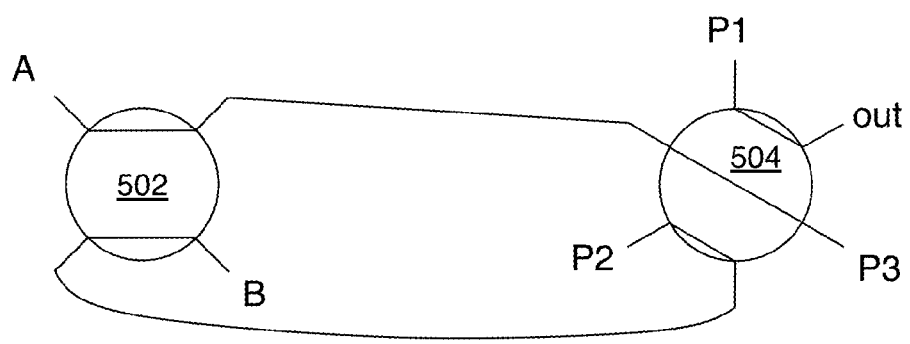

These considerations can be better appreciated by consideration of FIGS. 5A-F, which provide an example of a preferred gas flow switching approach for two gas sample inlets. Here gas flow control manifold 102 of FIG. 1A includes two rotary valves 502 and 504, connected as shown, where A and B are the gas inlets, P1, P2 and P3 are the gas sample storage chambers, and the port labeled "out" leads to the gas analysis instrument (not shown on FIGS. 5A-F). FIG. 5A show a first state of this manifold, FIG. 5B shows a second state of this manifold, FIG. 5C shows a third state of this manifold, FIG. 5D shows a fourth state of this manifold, FIG. 5E shows a fifth state of this manifold, and FIG. 5F shows a sixth state of this manifold.

In operation, the manifold is switched sequentially among these states as follows: 1→2→3→4→5→6→→1 . . . , with the sequence repeating as indicated. It is instructive to list what is happening during each of these states:
1) A→P1, B→P2, P3→out,
2) A→P1, B→P3, P2→out,
3) A→P2, B→P3, P1→out,
4) A→P2, B→P1, P3→out,
5) A→P3, B→P1, P2→out,
6) A→P3, B→P2, P1→out.

We begin by considering the playback of P2 in states 2 and 5. After the playback of state 2, P2 is effectively empty. Upon switching to state 3, P2 starts to fill with gas from inlet A (recording, part 1). Upon switching to state 4, P2 continues to fill with gas from inlet A (recording, part 2). In state 5, playback of P2 occurs, and because of the way the gas switching was performed, the contents of P2 at this time all relate to inlet A. In other words, between successive times a selected gas sample storage chamber (e.g., P2) is connected to the gas analysis instrument (i.e., states 2 and 5), the selected gas sample storage chamber is connected to a single one of the gas sample inlets (i.e., P2 is connected to inlet A in both states 3 and 4).

This consistency of sample acquisition is present for all gas sample storage chambers of this example. E.g., the playback of P1 in state 6 relates exclusively to inlet B because states 4 and 5 both consistently have inlet B connected to P1 for recording. As another example, the playback of P3 in state 1 relates exclusively to inlet A because the preceding two states (i.e., states 5 and 6) both consistently have inlet A connected to P3 for recording.

This preferred mode of operation can be provided in general as follows. The gas flow control manifold includes a first rotary valve having 2N ports and a second rotary valve having 2N+2 ports. The gas sample inlets are connected to alternating ports of the first rotary valve (leaving N ports of the first valve open). The N+1 gas sample storage chambers are connected to alternating ports of the second rotary valve (leaving N+1 ports of the second valve open). The N open ports of the first rotary valve are connected to N of the N+1 open ports of the second rotary valve (leaving one port of the second valve open). The gas analysis instrument is connected to this last open port of the second rotary valve. FIGS. 5A-F show an example of operation of this kind of gas flow control manifold.

Figure 6A:
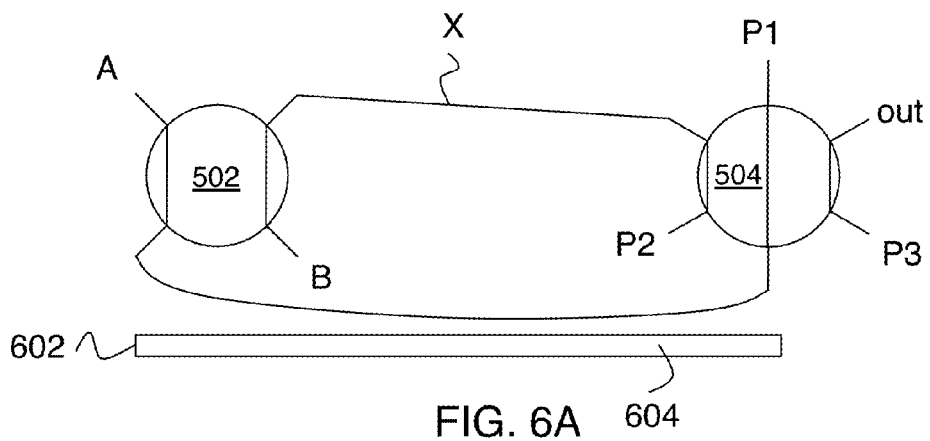
FIGS. 6A-C show a preferred switching timing approach as it relates to the example of FIGS. 5A-F.
Figure 6B:
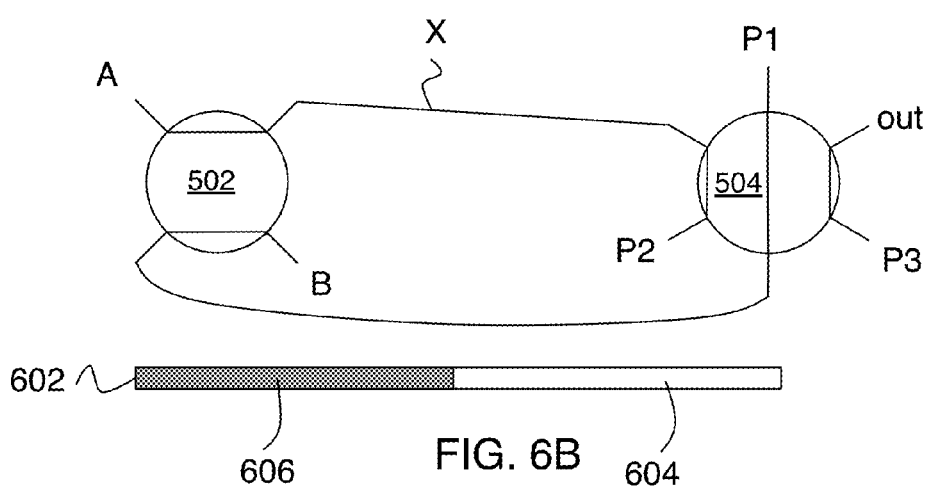
Figure 6C:
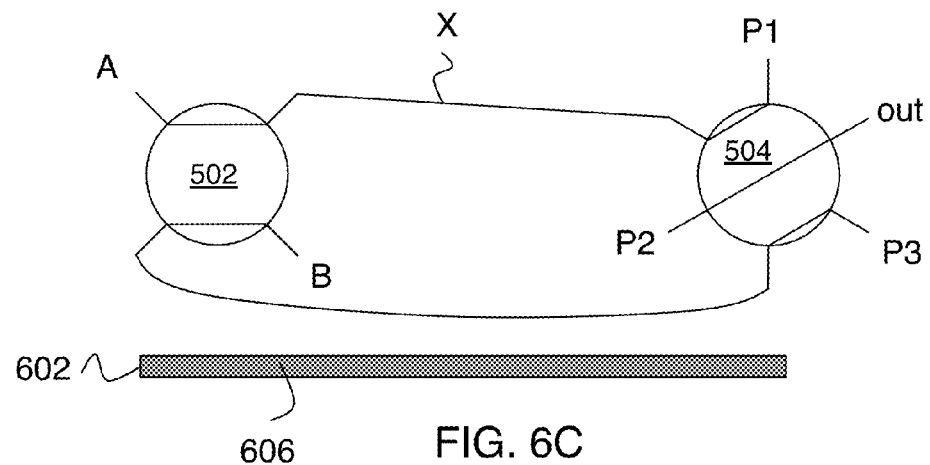
Figure 7A:
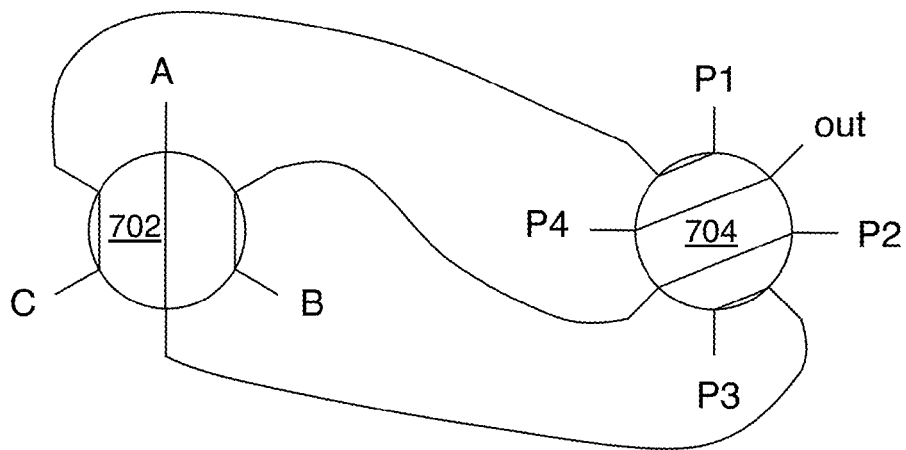
FIGS. 7A-H and 7J-M provide an example of a preferred gas flow switching approach for three gas sample inlets.
Figure 7B:
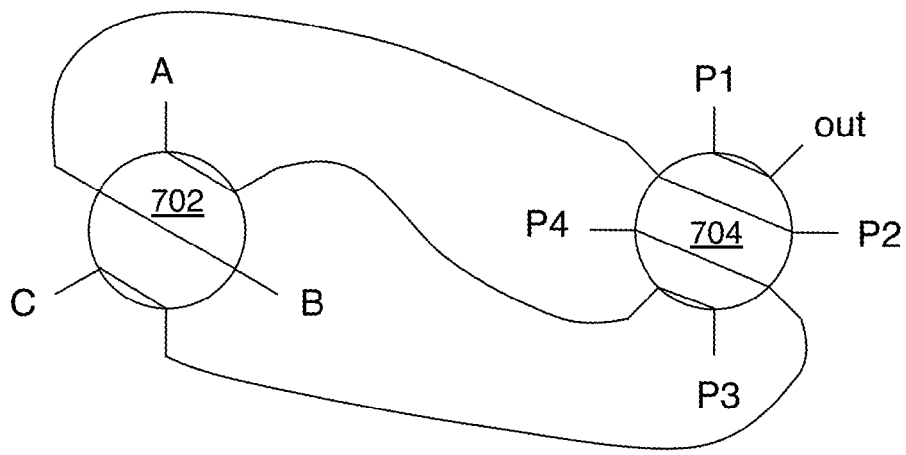
Figure 7C:
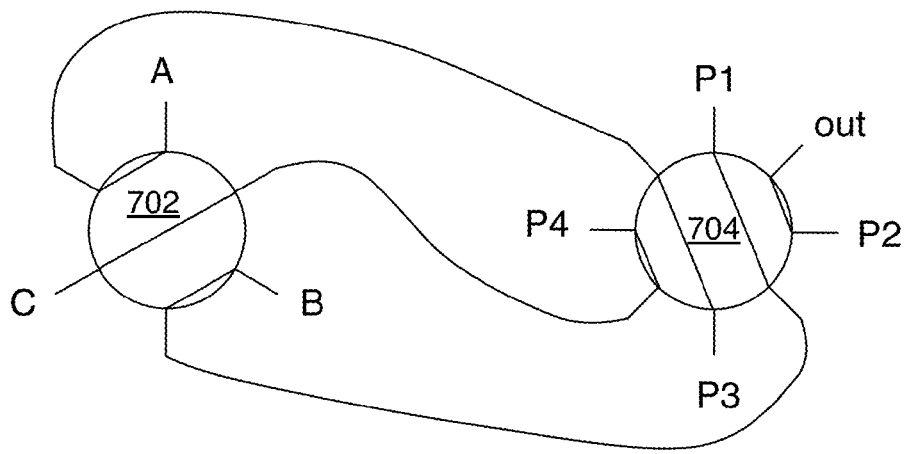
Figure 7D:
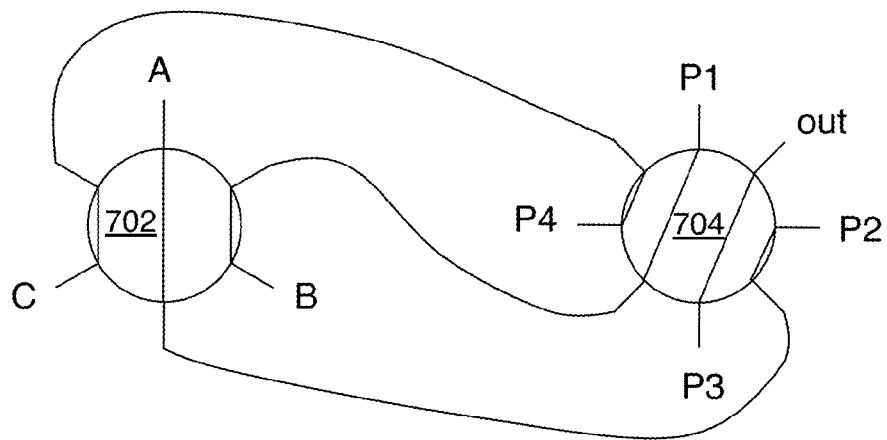
Figure 7E:
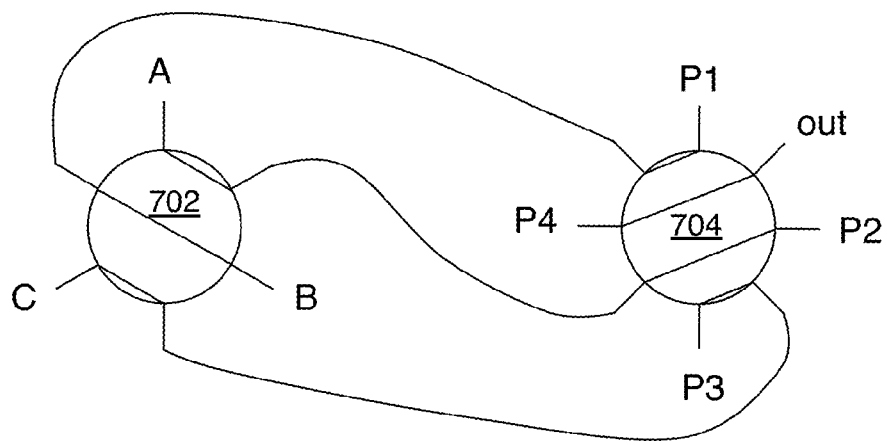
Figure 7F:
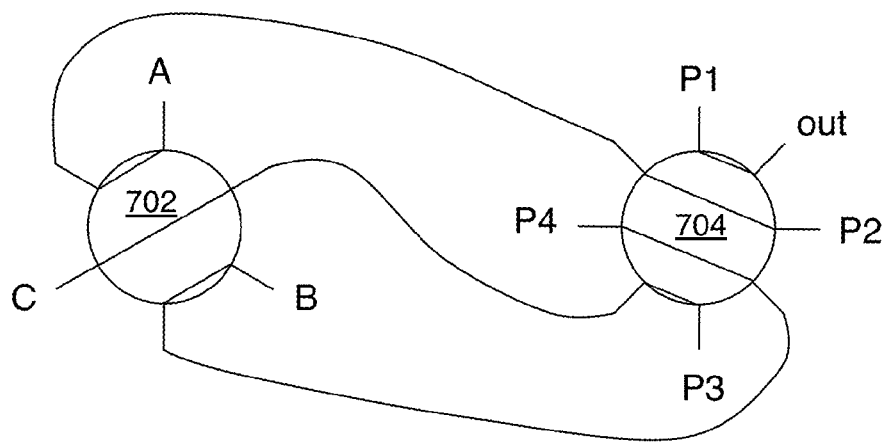
Figure 7G:
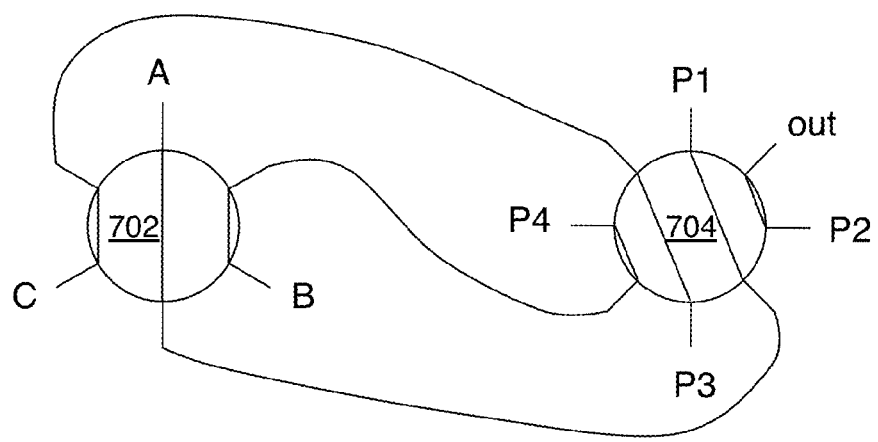
Figure 7H:
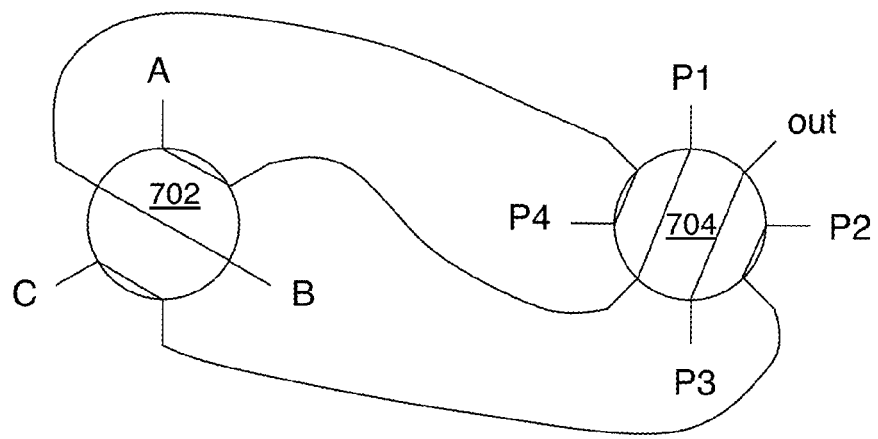
Figure 7J:
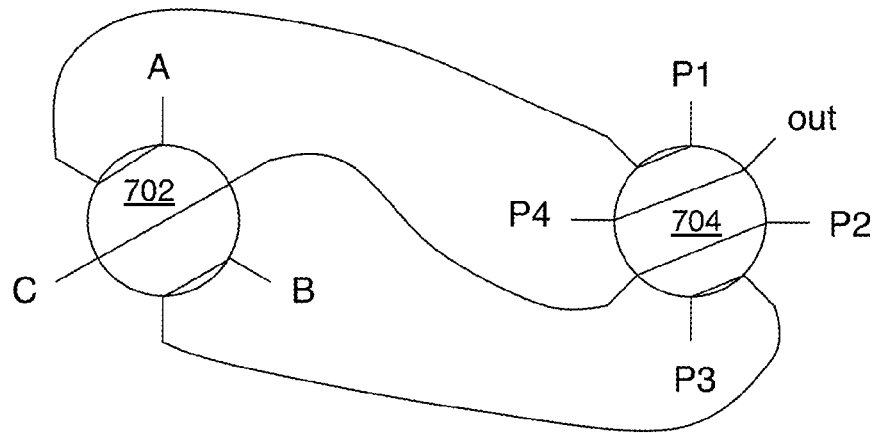
Figure 7K:
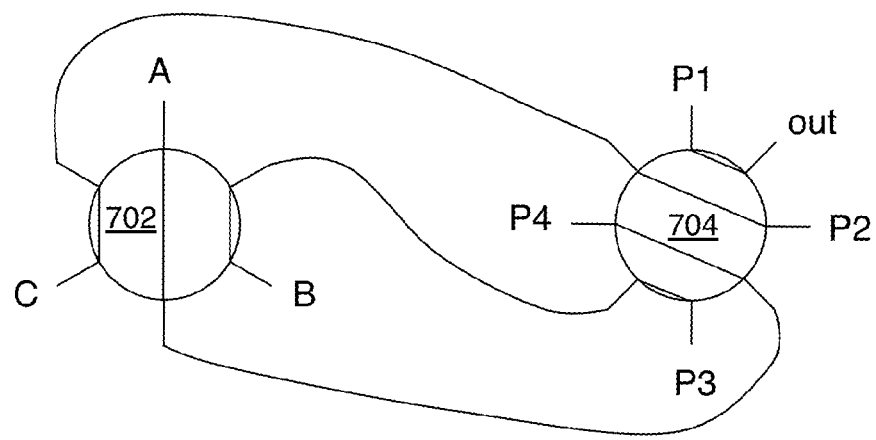
Figure 7L:
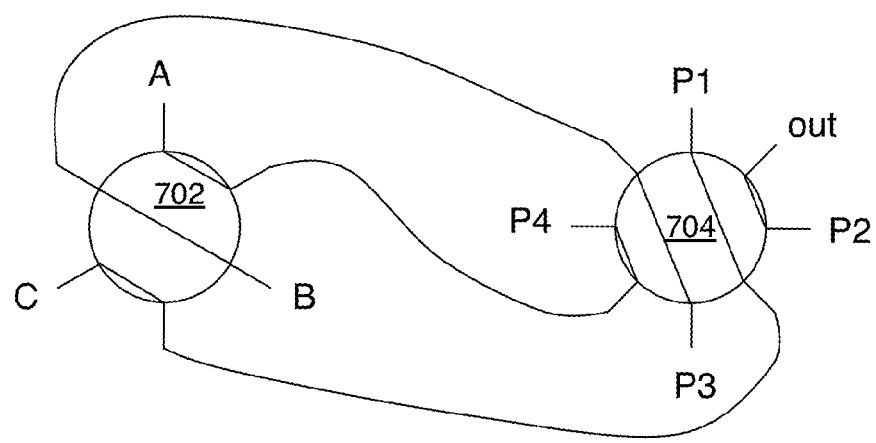
Figure 7M:
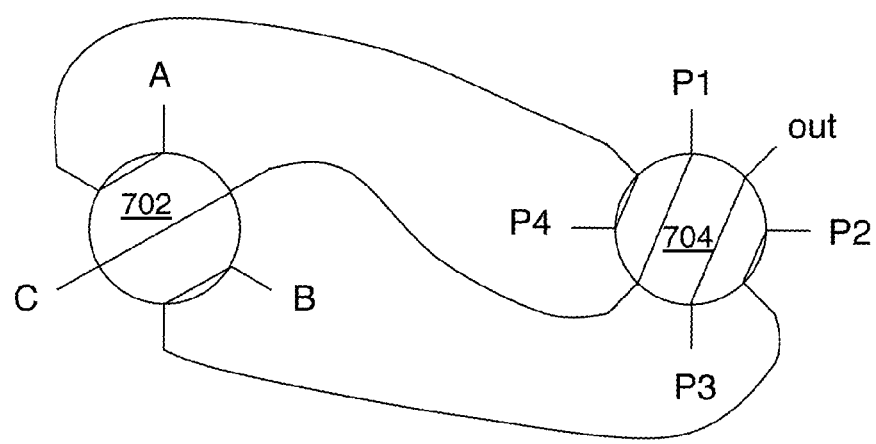

In embodiments like those of FIGS. 5A-F, it is undesirable to switch the two rotary valves at the same time. Instead it is preferred to switch the second valve (order 2N+2) later than the first valve (order 2N) such that the two switching times are separated by a switching delay time selected to account for the gas flow time between the first and second rotary valves. FIGS. 6A-C show how this works. FIG. 6A repeats the configuration of FIG. 5A, and schematically shows the state of the gas lines 602 between 502 and 504. In particular, gas lines 602 are shown as being filled up with a single constituent 604 (e.g., gas line X on FIG. 6A will have only gas from inlet B in it as constituent 604).

FIG. 6B shows the result of switching 502 to the position it has in FIG. 5B, but leaving the position of 504 unchanged. Here gas lines 602 have two constituents 604 and 606. For example, gas line X on FIG. 6B will have constituent 604 from inlet B and constituent 606 from inlet A. In the configuration of FIG. 6B, constituent 604 in gas line X (which is from inlet B) gets provided to gas sample storage chamber P2, which is correct behavior (i.e., it is consistent with FIG. 6A). However, this behavior will become incorrect when the transition between constituents 604 and 606 in gas lines 602 reaches second rotary valve 504.

Therefore, second rotary valve 504 is switched to the position shown on FIG. 6C at (or at least near) the time the transition between constituents 604 and 606 in gas lines 602 reaches second rotary valve 504. For consistency, it is preferred that connections between the first and second rotary valve have substantially equal lengths and diameters, so that transitions in all relevant gas lines take about the same amount of time to travel between the first rotary valve and the second rotary valve.

As indicated above, this approach for the gas flow control manifold can be extended to cases where N>2. FIGS. 7A-H and 7J-M provide an example of this gas switching approach for three gas sample inlets. Here 702 is the first rotary valve and 704 is the second rotary valve, connected as described above. The states (identified by figure reference) switch sequentially as follows: 7A→7B→7C→7D→7E→7F→7G→7H→7J→7K→7L→7M. Note that there are a total of twelve states, and that there is no FIG. 7I (or state 7I) to avoid possible confusion with the number 71. As can be seen from these figures, between successive times each gas sample storage chamber is connected to the gas analysis instrument, that gas sample storage chamber is connected to a single one of the gas sample inlets. For example, P4 is connected to the gas analysis instrument on FIGS. 7A and 7E, and is consistently connected to gas inlet C on FIGS. 7B, 7C and 7D.

The invention claimed is:

1. Apparatus for gas sample acquisition and analysis, the apparatus comprising:
   N gas sample inlets disposed at spaced apart locations, wherein N is an integer greater than or equal to two;
   N+1 gas sample storage chambers;
   a gas analysis instrument; and
   a gas flow control manifold capable of connecting the gas sample storage chambers to the gas sample inlets and to the gas analysis instrument;
   wherein the gas flow control manifold is capable at least of connecting any of the gas sample storage chambers to the gas analysis instrument while at least one other of the gas sample storage chambers is connected to one of the gas sample inlets.

2. The apparatus of claim 1, wherein the apparatus is configured such that gas is admitted from the gas sample inlets to the gas sample storage chambers at an acquisition flow rate, wherein gas is admitted from a selected one of the gas sample storage chambers to the gas analysis instrument at an analysis flow rate, and wherein the acquisition flow rate and the analysis flow rate differ by 40% or more of the acquisition flow rate.

3. The apparatus of claim 2, wherein the analysis flow rate is faster than the acquisition flow rate.

4. The apparatus of claim 2, wherein the analysis flow rate is slower than the acquisition flow rate.

5. The apparatus of claim 1, wherein the gas sample storage chambers are configured as tubes having a length to diameter ratio of 100 or more.

6. A method for gas analysis, the method comprising:
   providing N gas sample inlets disposed at spaced apart locations, wherein N is an integer greater than or equal to two;
   providing N+1 gas sample storage chambers;
   providing a gas analysis instrument; and
   providing a gas flow control manifold capable of connecting the gas storage chambers to the gas sample inlets and the gas analysis instrument;
   wherein the gas flow control manifold is capable at least of connecting any of the gas sample storage chambers to the gas analysis instrument while at least one other of the gas sample storage chambers is connected to one of the gas sample inlets.

7. The method of claim 6, further comprising reconstructing a common time axis for two or more gas samples from switching and flow conditions of the gas flow control manifold, and known connection molar volumes.

8. The method of claim 6, wherein the gas flow control manifold is configured and operated such that between successive times a selected gas sample storage chamber is connected to the gas analysis instrument, the selected gas sample storage chamber is connected to a single one of the gas sample inlets.

9. The method of claim 8, wherein the gas flow control manifold includes a first rotary valve having 2N ports and a second rotary valve having 2N+2 ports, wherein the gas sample inlets are connected to alternating ports of the first rotary valve, wherein the gas sample storage chambers are connected to alternating ports of the second rotary valve, wherein N ports of the first rotary valve not connected to gas sample inlets are connected to N ports of the second rotary valve not connected to the gas sample storage chambers, and wherein the gas analysis instrument is connected to a port of the second rotary valve not connected to the first rotary valve or to a gas sample storage chamber.

10. The method of claim 9, further comprising:
first switching the first rotary valve; and
second switching the second rotary valve, wherein a time of the second switching is later than a time of the first switching by a switching delay time;
wherein the switching delay time is selected to account for gas flow time between the first and second rotary valves.

11. The method of claim 10, wherein connections between the first and second rotary valves have substantially equal lengths and diameters.

\* \* \* \* \*